(12) United States Patent
Abbiati

(10) Patent No.: US 6,495,148 B1
(45) Date of Patent: Dec. 17, 2002

(54) REACTION PRODUCTS OF HYALURONIC ACID AND NATURAL AMINO ACIDS AND THEIR USE IN COSMETIC AND PHARMACEUTICAL COMPOSITIONS

(76) Inventor: Giuliana Abbiati, Via Pontaccio, Milan (IT), 20121

( * ) Notice: Subject to any disclaimer, the term of this patent is extended or adjusted under 35 U.S.C. 154(b) by 0 days.

(21) Appl. No.: 09/744,685

(22) PCT Filed: Jul. 29, 1999

(86) PCT No.: PCT/IT99/00250

§ 371 (c)(1),
(2), (4) Date: Jan. 29, 2001

(87) PCT Pub. No.: WO00/08061

PCT Pub. Date: Feb. 17, 2000

(30) Foreign Application Priority Data

Aug. 5, 1998 (IT) .......................................... MI98A1836

(51) Int. Cl.[7] .............................. A61K 7/00; A61K 7/48; A61K 31/195
(52) U.S. Cl. ........................ 424/401; 424/78.06; 424/59; 514/62; 514/54; 514/2; 514/887; 514/861; 536/20; 536/21
(58) Field of Search .......................... 514/62, 887, 861, 514/54; 424/401, 78.06, 59; 536/21, 20

(56) References Cited

U.S. PATENT DOCUMENTS

| | | | |
|---|---|---|---|
| 4,937,270 A | 6/1990 | Fox et al. | |
| 5,527,893 A | 6/1996 | Burns et al. | |
| 5,702,688 A | * 12/1997 | Yu et al. | .................. 424/59 |
| 5,760,200 A | * 6/1998 | Miller et al. | .................. 536/21 |

FOREIGN PATENT DOCUMENTS

| | | |
|---|---|---|
| WO | WO95/24429 | 9/1995 |

* cited by examiner

Primary Examiner—Jose' G. Dees
Assistant Examiner—Mina Haghighatian
(74) Attorney, Agent, or Firm—Nixon & Vanderhye P.C.

(57) ABSTRACT

New high molecular weight salts of hyaluronic acid, especially salts having as a counterion a natural amino acid are described. They are prepared starting from high molecular weight hyaluronic acid or its salts. These high molecular weight salts of hyaluronic acid are advantageously employed in cosmetic and pharmaceutical uses.

21 Claims, No Drawings

REACTION PRODUCTS OF HYALURONIC ACID AND NATURAL AMINO ACIDS AND THEIR USE IN COSMETIC AND PHARMACEUTICAL COMPOSITIONS

This application is the U.S. national phase of international application PCT/IT99/00250, filed Jul. 29, 1999, which designated the U.S.

The present invention relates to new derivatives of hyaluronic acid, a process for their preparation and the cosmetic or pharmaceutical compositions containing such products.

BACKGROUND OF THE INVENTION

Hyaluronic acid is a mucopolysaccharide that is present almost in each part of a living organism and in particular in the skin. Chemically, hyaluronic acid is formed by straight polymer chains having a molecular weight ranging from hundreds thousand to millions dalton, including repeated disaccharid units constituted by N-acetyl glucosamine and glucoronic acid bound to each other by glucosidic bonds. Hyaluronic acid has the capacity of binding high amounts of water coming from the capillary network, necessary to keep in a solution form the catabolites, electrolytes and gases that spread from the capillaries to the cells and vice-versa, through the interstitial fluid. This phenomenon is of the essential to maintain the skin elastic and in a gelatinous physical condition. Hence, hyaluronic acid has a basic role in the control of the diffusion of nutrients, hormones, vitamins and inorganic salts of the connective tissue and in the removal of metabolism wastes which may give rise to reactions of an inflammatory type. As age increases, the amount of hyaluronic acid present in the organism decreases as well as its polymerization level, which results in a reduction in retained water, the skin shows alterations of its physical condition and undergoes an aging process that causes an increase in the fibrous part with respect to the elastic one.

There are at present known cosmetic preparations that are mainly used as moisturizers or age retarding preparations, based on low molecular weight hyaluronic inorganic salts. Such preparations have the drawback of utilizing low molecular weight hyaluronic acid, which is much less effective compared to high molecular weight hyaluronic acid. On the other hand, high molecular weight hyaluronic acid is scarcely soluble, which creates severe technical problems in the preparation of cosmetic and pharmaceutical formulations. As a consequence, the need is still felt of providing derivatives of hyaluronic acid having a high effectiveness in the cosmetic and pharmaceutical field, and having also chemical-physical characteristics such as to allow their use in different types of formulations. The present invention relating to high molecular weight new derivatives of hyaluronic acid solves these problems.

BRIEF SUMMARY OF THE INVENTION

From one of these aspects, the present invention relates to new salts between high molecular weight hyaluronic acid and at least one natural amino acid. Preferred salts are those wherein the amino acid is selected from among lysine, arginine, methionine or aspartic acid. Particularly advantageous is lysine yaluronate which we gave the invention name Yalyse and which will be indicated in the future by the mark "YALYSE".

By the expression "high molecular weight hyaluronic acid", there is intended to indicate a hyaluronic acid having a molecular weight comprised between 1.5 and 3 million dalton.

The use of these new derivatives of hyaluronic acid in the cosmetic and pharmaceutical field provides remarkable advantages with respect to the known art. First of all, high molecular weight hyaluronic acid has the capacity of binding water amounts much higher than low molecular weight hyaluronic acid, promoting thereby a better diffusion of the dissolved substances and a greater elasticity of the skin. Besides this, the compounds of the present invention are constituted by hyaluronic acid salts with a counterion that can exercise a synergetic action with the yaluronate. In fact, as is known, amino acids carry out an essential role in the formation of special substances of skin physiology, such as melanin and keratin.

Of particular importance is lysine, which is basic in the biosynthesis of melanin, as well as the collagen of elastin and reticulin which are the main proteic skin components. The derivatives of the present invention are therefore capable of markedly reducing skin aging through an increase moisturizing of the dermis, a promoted cellular recycling and a stimulation of the synthesis of elastin as well as of free radicals.

From another of its aspects, the present invention relates to a process for the preparation of salts selected from among hyaluronic acid and at least a natural amino acid, characterized in that hyaluronic acid or a salt thereof is caused to react with at least a natural amino acid, in the form of a free base or in a salified form, respectively.

According to an advantageous aspect, the present invention relates to a process for the preparation of lysine hyaluronate, characterized in that sodium hyaluronate is reacted with lysine hydrochloride. Preferably, such reaction is carried out by suspending sodium hyaluronate in water and stirring until it gels before adding lysine hydrochloride.

The preparation reactions of the salts subject matter of the present patent application may be carried out using a stochiometric amount of the reagents or an excess of either component, in which latter case one obtains the salt and an excess reagent co-ordination through hydrogen bonds. By the expression "stochiometric amounts of the reagents" there is intended to indicate that the number of amino acid moles used is equal to the number of the carboxy functions that are present in hyaluronic acid.

The possibility of varying the ratio of acid moles to amino acid moles allows to modulate the characteristics of the products obtainable as a function of the desired properties.

Organic molecules of various type may be coordinated to the products obtained according to the aforesaid processes by means of hydrogen bonds.

This allows to obtain end products having variable chemical-physical and pharmacological properties.

From another of its aspects, the present invention relates to the use of new high molecular weight hyaluronic acid salts in the cosmetic field.

From a further aspects the present invention relates to the use of the new high molecular weight hyaluronic acid salts as medicaments.

The active principles of the present invention are adapt to be formulated with suitable excipients, for instance those usually utilized is the cosmetic field, such as bee-wax, jujube oil, isostearyl isostearate, fatty acid, triglycerides, propylen glycol, lauryl alcohol, and hydroxypropylmethyl cellulose. Stabilizers, antioxidants, and preservatives, either individually or combined with each other, may be added to these active principles. Suitable stabilizers include Acepur K, Abiol, Prevan, Fondix G, BHA, BHT. Suitable antioxidants include butylhydroxyanisole, citric acid, tocopherol, sodium thiophosphate. Suitable preservatives include p-hydroxybenzoic acid esters or imidazolidinyl urea.

A preferred composition of the invention is in the one that comes in the form of an emulsion. Emulsions containing 1% to 5% lysine hyaluronate (Yalyse) are particularly preferred. Such compositions, either in the pure form or in the form of lyophilized sheets, are used in the treatment of burn wounds, decubitus ulcers, venous ulcers, and in all cicatrization processes. They may be also advantageously used in aesthetic surgery, especially following epidermis abrasion laser therapy interventions, in order to achieve a quicker and optimum re-epithelization.

Another preferred composition of the present invention in the one that comes in the form of a lotion. Particularly advantageous are the lotions comprising 1% to 7% arginine hyaluronate, possibly mixed with glycolic acid and carrier substances and suitable excipients compatible with the type of utilization desired. Such lotions may be employed in alopecia cases due to excess sebum production, in allergy-based scalp hyperkeratoses, and in dandruff persistent cases.

A further type of preferred composition of the present invention is the one that comes in the form of a cream. Particularly advantageous are creams based on 1% to 7% lysine hyaluronate (Yalyse), possibly mixed with one or more substances selected from among vitamin A, vitamin E, ascorbic acid, cogic acid, allantoin, echinaceous calendula, "centella", horsetail, persea, propolis, aloe, cera alba, arachis, zea mays, horse chestnut, ginko biloba, jujube, shea butter, bee-wax, hazelnut, sunflower, and with excipients compatible with its specific utilization. Thanks to their moisturizing action, such creams are particularly useful in reducing the process of skin-aging, in the treatment of wrinkles, dryness, opacity, and in promoting skin elasticity and luminosity. These creams may also be used as protectors in photodermatosis, as anti-erythema and, together with cogic acid or hydroquinone, in the treatment of senile spots.

From a last aspect, the invention relates to the use of new high molecular weight hyaluronic acid salts for the preparation of medicaments suitable for the treatment or prevention of a pathologic condition selected from among psoriasis, eczema, ichthyiosis, postactinic radiodermatosis, hemorrhoids, proctitis, hemorrhagic proctitis, atopic dermatitis, trophic ulcers and decubitus ulcers, sudamina, epidermophytosis or, generally, in the cases of prurigo. In these cases, the pharmaceutical compositions may possibly also include one or more substances selected from among salicylic acid, ascorbic acid or retynyl palmitate.

In the following, some examples of embodiments of the present invention are reported, only by way of non-limiting example.

DETAILED DESCRIPTION OF THE INVENTION

Process for the Preparation of Lysine Hyaluronate 1 g sodium hyaluronate (corresponding to 0.945 g hyaluronic acid) is reacted with 0.455 g lysine hydrochloride (0.364 g free base lysine), obtaining 1.31 g lysine hyaluronate and 0.145 g NaCl.

The preparation of the product takes place according to the following steps:

a) preparation of gel by mixing sodium hyaluronate with water;

b) preparation of lysine hydrochloride;

c) addition of lysine hydrochloride to sodium hyaluronate gel;

d) freeze-drying of the product.

Gelation of Sodium Hyaluronate 10 g sodium hyaluronate are suspended under stirring in 300 ml of deionized water, up to full gelation.

The product is clear, colorless, homogeneous and free from clots. The gel obtained has a pH of 6.6.

The hyaluronic acid/water ratios are indicative; greater water amounts may be used (either at the start or upon completion of the product), should one wish not to proceed to drying or freeze-drying the product, utilizing instead directly the gel, in order to obtain a product having the most suitable physical properties (for instance, viscosity).

PreDaration of Iysine Hydrochloride 7.3 g 50% free base lysine are diluted in 20 ml water (corresponding to 3.65 g lysine), and 25 ml HCL 1N (corresponding to 0.91 g HCl) are added under stirring. Before the addition of the acid, the solution has a pH of 9.9, upon completion of the acidification, the pH is of 5.7.

Synthesis of Lysine Hyaluronate

Lysine hydrochloride is added to the previously prepared sodium hyaluronate gel, slowly and under stirring; once the addition is completed, stirring is maintained for about 1 hour, to obtain the complete homogenization of the product. The product has a pH of 6.5.

Should one wish to modify the pH of the product, an acid or a base is added under the control of a pH-meter, until the pH desired is obtained.

Other organic molecules may be added to the product obtained, which are coordinated by means of hydrogen bonds.

The product is allowed to rest overnight in a freezer, and the following day it is freezedried or vacuum dried.

Following the same process, it is possible to prepare: arginine hyaluronate, methionine hyaluronate, and aspartic acid hyaluronate.

The synthesis diagrams for the reactions carried out starting from non-salified products are shown hereunder.

LYSINE HYALURONATE

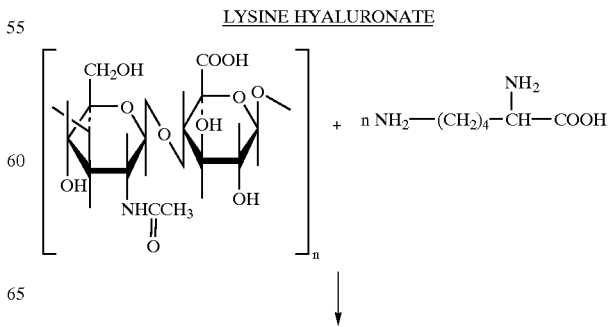

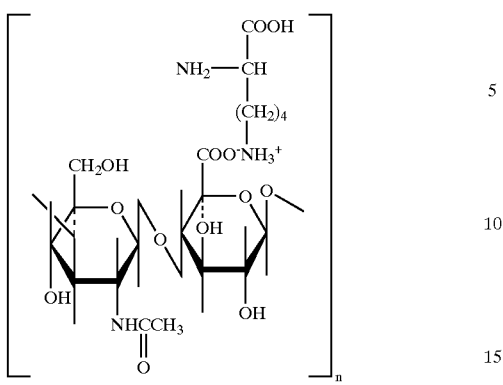
ARGININE HYALURONATE
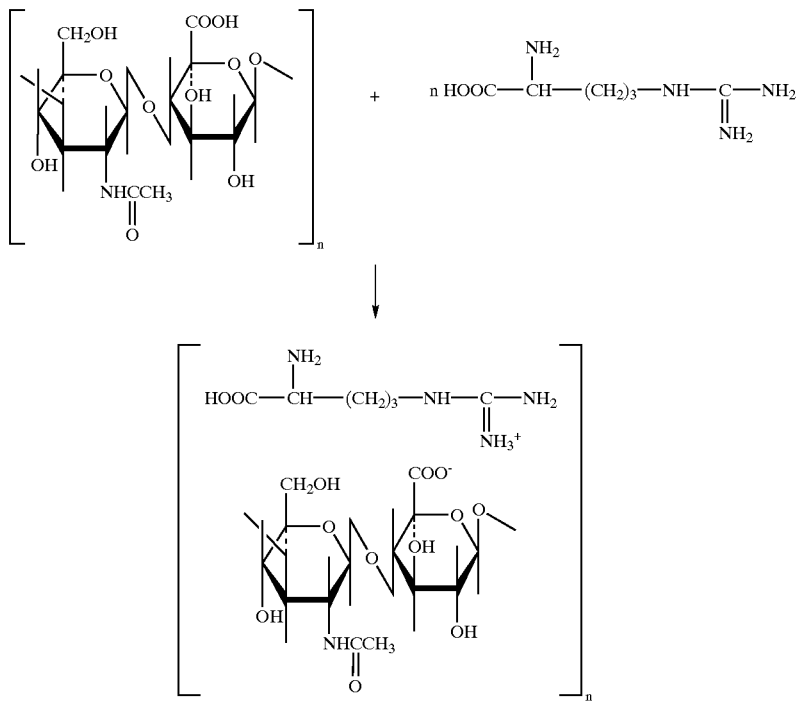
METHIONINE HYALURONATE
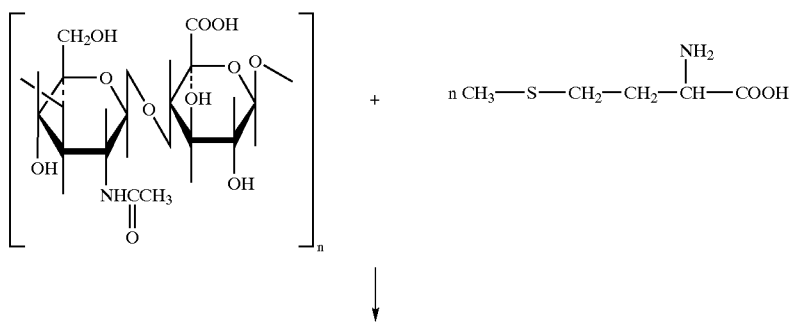

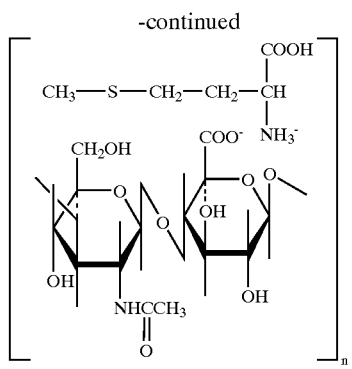

ASPARTIC ACID HYALURONATE

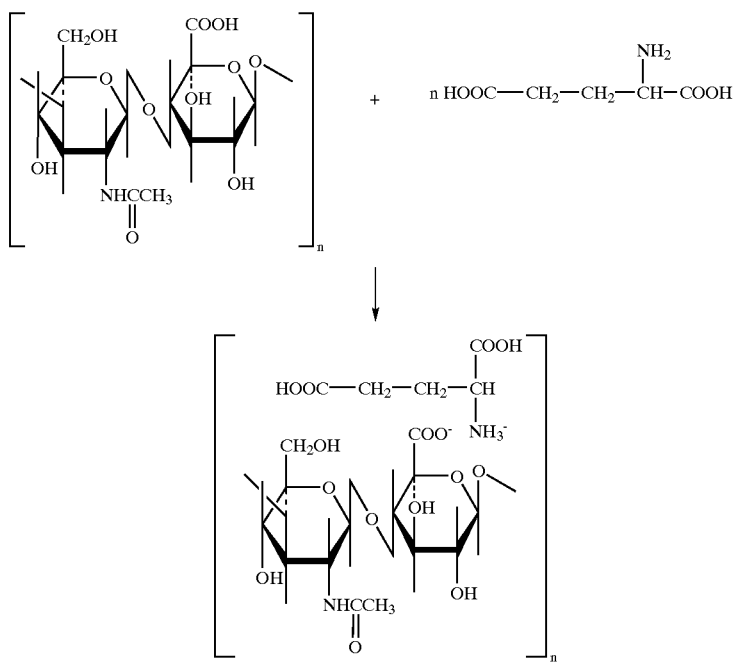

Preparation of the Scalp Lotion

The preserving substances are vacuum loaded in a turboemulsifier at a temperature of 80° C.

Afterwards, the remaining matters are introduced under stirring one by one, except for arginine hyaluronate.

After 15' mixing at a constant speed, the temperature is cooled to 40° C., arginine hyaluronate is added and mixing is continued until the temperature of 25° C. is reached.

The obtained mixture is filtered with a polycarbonate filter with 0.45 μ holes.

The end formulation has the following composition:

| DEIONIZED WATER | Q.S. | 100 |
|---|---|---|
| GLYCOLIC ACID | % | 5 |
| ARGININIE HYALURONATE | % | 3 |
| UNDECYLENAMIDE DEA | % | 1 |
| PG-HYDROXYETHYL CELLULOSE | % | 0.9 |
| COCODINIUM CHLORIDE | % | 0.75 |
| SODIUM HYDROXIDE | % | 0.75 |
| POLYQUATERNARIUM-10 | % | 0.6 |
| ZINC P.C.A. | % | 0.3 |
| IMIDAZOLIDINYL UREA | % | 0.3 |
| BENZOPHENONE | % | 0.05 |

Preparation of Age-retarding Cream

All the excipients are vacuum loaded in two turboemulsifiers at a temperature of 80° C.

Emulsifier-A)—all water-soluble excipients.

Emulsifier-B)—all oily excipients.

Except for: lysine hyaluronate, elastin, collagen, tocopherol and fragrance. Both meltings are stirred until the temperature reaches 80° C.

Now both meltings are united and mixed for 15' at a constant speed, lowering temperature to 40° C. Now the matters left by side are added, and stirring is continued until the temperature reaches 25° C.

The end formulation has the following composition:

| | | | |
|---|---|---|---|
| DEIONIZED WATER | Q.S. | | 100 |
| PROPYLEN GLYCOL | | | 5 |
| GLYCERYL STEARATE | | % | 5 |
| OCTYL STEARATE | | | 3.5 |
| CETEARYL ALCOHOL | | % | 3.5 |
| LYSINE HYALURONATE | | | 3 |
| STEARETH-30 | | % | 2.7 |
| CETETH-2 | | | 2.7 |
| SHEA BUTYRUM | | % | 2.4 |
| ELASTIN | | % | 1 |
| SOLUBLE COLLAGEN | | | 1.5 |
| OLEA EUROPEA CALENULA OFFICINALIS | | | 1 |
| PERSEA GRATISSIMA | | % | 1 |
| CERA ALBA | | | 1 |
| TRIISOSTEARIN | | % | 1 |
| TOCOPHEROL (Vit. E) | | | 1 |
| RETYNYL PALMITATE (Vit. A) | | | 0.3 |
| PHENOXYETHANOL | | | 0.3 |
| ASCORBIC ACID (Vit. C) | | | 0.2 |
| FRAGRANCE | | | 0.2 |
| BHA | | | 0.1 |
| POLYSORBATE 20 | | | 0.1 |
| DICHLOROBENZYL ALCOHOL | | | 0.1 |
| DEHYDROACETIC ACID | | | 0.1 |
| TRIETHANOLAMINE | | | 0.1 |
| SODIUM METHYL PARABEN | | | 0.09 |
| SODIUM PROPYL PARABEN | | | 0.03 |
| ARACHIS HYPOGAEA | | | 0.01 |
| BHT | | | 0.0003 |
| PROPYL GALLATE | | | 0.0003 |
| CITRIC ACID | | | 0.0001 |
| PREPARATION OF THE EMULSION | | | |

All the excipients are vacuum loaded in a turboemulsifier at a temperature of 80° C., except for lysine hyalurate. The whole is turbo-stirred for 15', at a constant speed.

Afterwards, always under stirring, the temperature is cooled to 40° C.

When this temperature has been reached, lysine hyalurate is added and mixing is continued slowly until the emulsion is cooled and a temperature of 28° C. is reached.

The obtained mixture is then submitted to bacteriologic control.

The end formulation has the following composition:

| | | | |
|---|---|---|---|
| DEIONIZED WATER | Q.S. | | 100 |
| ARGININIE HYALURONATE | | % | 3 |
| PROPYLEN GLYCOL | | % | 1.3 |
| RETYNYL PALMITATE (Vit. A)) | | % | 0.3 |
| IMIDAZOLIDINYL UREA | | % | 0.3 |
| ASCORBIC ACID (Vit. C) | | % | 0.2 |
| SODIUM METHYL PARABEN | | % | 0.15 |
| SODIUM PROPYL PARABEN | | % | 0.09 |

What is claimed is:

1. A salt of hyaluronic acid ionically bonded to at least one natural amino acid as a counterion wherein the hyaluronic acid has a molecular weight of 1.5 to 3 million Dalton.

2. The salt of claim 1, wherein said amino acid is selected from the group consisting of lysine, arginine, methionine and aspartic acid.

3. Lysine hyaluronate having the following formula

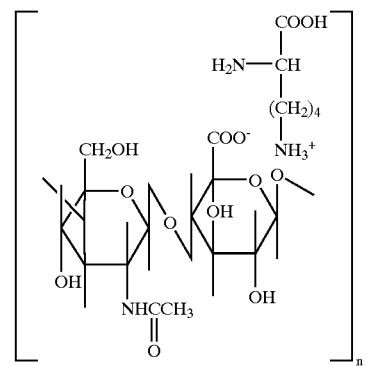

4. A process for the preparation of a salt according to claim 1, wherein hyaluronic acid or a salt thereof is reacted with at least one free or salified amino acid.

5. The process for the preparation of lysine hyaluronate of claim 3, wherein sodium hyaluronate is reacted with lysine hydrochloride.

6. The process of claim 5, wherein the sodium hyaluronate is suspended in water and stirred to gelification before addition of lysine hydrochloride.

7. A cosmetic or pharmaceutical composition comprising at least one salt of claim 1.

8. The composition of claim 7, in the form of an emulsion.

9. The composition of claim 8 comprising 1 to 5% of lysine hyaluronate.

10. The composition of claim 9, further comprising deionized water, propylene glycol, retynyl palmitate, imidazolydinyl urea, ascorbic acid, sodium methylparaben and sodium propylparaben.

11. Method for treating decubitus ulcers, venous ulcers or cicatrization processes which comprises administering to a subject a salt of claim 1.

12. The composition of claim 7, in the form of a lotion.

13. The composition of claim 12, comprising 1% to 7% of arginine hyaluronate.

14. The composition of claim 13, comprising deionized water, glycolic acid, undecylenee urea, PG-hydroxyethyl cellulose, cocodinium chloride, sodium hydroxide, polyquaternarium-10, p.c.a. zinc, imidazolydinyl urea and benzophenone.

15. Method for treating alopecia, scalp hyperkeratoses or dandruff which comprises topically administering to a subject a composition according to claim 12.

16. The composition of claim 7 the form of a cream.

17. The composition of claim 16 comprising lysine hyaluronate.

18. The composition of claim 17 comprising:

| | | |
|---|---|---|
| deionized water | q.s. | 100 |
| propylene glycol | % | 5 |
| glyceryl stearate | % | 5 |
| octyl stearate | % | 3.5 |
| cetearyl alcohol | % | 3.5 |
| lysine hyaluronate | % | 3 |
| steareth-30 | % | 2.7 |
| ceterh-2 | % | 2.7 |
| shea buryrum | % | 2.4 |
| elastin | % | 1 |
| soluble collagen | % | 1.5 |
| olea europea calendula officinalis | % | 1 |

-continued

| | % | |
|---|---|---|
| persea gratissima | % | 1 |
| cera alba | % | 1 |
| triisostearin | % | 1 |
| tocopherol (vit. e) | % | 1 |
| retynyl palmitate (vit. a) | % | 0.3 |
| phenoxyethanol | % | 0.3 |
| ascorbic acid (vit. c) | % | 0.2 |
| fragrance | % | 0.2 |
| bha | % | 0.1 |
| polysorbate 20 | % | 0.1 |
| dichlorobenzyl alcohol | % | 0.1 |
| dehydroacetic acid | % | 0.1 |
| triethanolamine | % | 0.1 |
| sodium methyl paraben | % | 0.09 |
| sodium propyl paraben | % | 0.03 |
| arachis hypogaea | % | 0.01 |
| bht | % | 0.0003 |
| propyl gallate | % | 0.0003 |
| citric acid | % | 0.0001. |

19. Method for treating wrinkles, skin dryness, opacity or aging processes which comprises administering to a subject a composition according to claim 16.

20. Method for treating a pathologic condition selected from the group consisting of psoriasis, eczema, ichthyiosis, postactinic radiodermatosis, hemorrhoids, proctitis, hemorrhagic proctitis, atopic dermatitis, trophic ulcers, decubitus ulcers, sudamina, epidermophytosis and prurigo, which method comprises administering to a subject in need of same a salt of claim 1.

21. The composition of claim 7 which further contains at least one of salicylic acid, ascorbic acid and retynyl palmitate.

* * * * *